United States Patent [19]

Tangney et al.

[11] Patent Number: 4,507,455
[45] Date of Patent: Mar. 26, 1985

[54] SILICONES BEARING ACYLATED DIAMINOHYDROCARBYL RADICALS AND METHOD THEREFOR

[75] Inventors: Thomas J. Tangney; Maris J. Ziemelis, both of Midland, Mich.

[73] Assignee: Dow Corning Corporation, Midland, Mich.

[21] Appl. No.: 609,380

[22] Filed: May 11, 1984

[51] Int. Cl.$^3$ ............................................. C08G 77/04
[52] U.S. Cl. ....................................... 528/26; 528/35; 528/38; 556/419; 556/421
[58] Field of Search ..................... 528/26, 35, 38; 556/419, 421

[56] References Cited

U.S. PATENT DOCUMENTS

| 2,929,829 | 3/1960 | Morehouse | 260/448.2 |
| 3,209,053 | 9/1965 | Gilkey et al. | 260/824 |
| 3,440,261 | 4/1969 | Saam | 260/448.2 |
| 3,702,860 | 11/1972 | Krahnke | 260/448.8 |
| 3,772,351 | 11/1973 | Krahnke | 260/448.2 |
| 3,956,353 | 5/1976 | Plueddemann | 260/448.8 |
| 4,075,167 | 2/1978 | Takemizawa et al. | 260/46.5 |
| 4,390,713 | 6/1983 | Martin | 556/418 |

Primary Examiner—Melvyn I. Marquis
Attorney, Agent, or Firm—George A. Grindahl

[57] ABSTRACT

Aminofunctional siloxanes, such as siloxanes bearing ethylenediamine-substituted hydrocarbon radicals, have their amine functionality fully modified by reaction with a monocarboxylic acid anhydride. The modifying functionality includes complete diamide or amide-amine salt formation. The amide-amine salt functionality can further be converted to a mixture of diamide and amide-amine functionality, if desired. The modified aminofunctional siloxanes have utility as components in hair care compositions, textile treating compositions and moldable polymeric compositions.

33 Claims, No Drawings

SILICONES BEARING ACYLATED DIAMINOHYDROCARBYL RADICALS AND METHOD THEREFOR

BACKGROUND OF THE INVENTION

This invention relates generally to organopolysiloxane compounds which contain modified silicon-bonded N-(aminohydrocarbyl)-aminohydrocarbyl radicals (herein also diamine radicals) and to a process for their preparation. More specifically, the present invention relates to organopolysiloxane compounds which contain silicon-bonded acylated diamine radicals and to an acylating process for their preparation.

Organopolysiloxane compounds which contain silicon-bonded N-(aminohydrocarbyl)-aminohydrocarbyl radicals are well known in the organosilicon art. They have found utility as precursors to other organopolysiloxane compounds, as components in textile treating baths and hair care compositions and as curable compositions, owing in large part to the chemical reactivity of the diamine radicals that are present therein. However, for many uses the chemical reactivity of said diamine radicals is not suitable and attempts to modify the diamine radicals have been made.

Gilkey et al. and Krahnke have reacted urea with an organopolysiloxane bearing diamine radicals to provide organopolysiloxanes bearing various degrees of uriedo-substitution. U.S. Pat. Nos. 3,209,053; 3,702,860 and 3,772,351. The resulting organopolysiloxanes were useful as a reactive component in textile-treating formulations that also contained urea-based resins.

Martin, U.S. Pat. No. 4,390,713, teaches that amino-functional polysiloxanes can be reacted with a cyclic anhydride or a dicarboxylic acid to provide carboxylic acid-functional polysiloxanes.

Plueddemann, U.S. Pat. No. 3,956,353, teaches that certain N-(aminoethyl)-aminoalkyl-substituted silanes can be reacted with 1 or 2 mols of a dicarboxylic acid anhydride to provide a zwitterion-substituted or a diacidamide-substituted silane, respectively.

Takemizawa et al., U.S. Pat. No. 4,075,167, have disclosed the reaction of a substituted maleic anhydride with an aminohydrocarbyl-substituted or an N-(aminoethyl)-aminohydrocarbyl-substituted silane or siloxane. In the later stages of this reaction, the use of an aliphatic acid anhydride in catalytic amounts or in reaction-medium amounts is allowed. The resulting maleimido group-containing organosilicon compounds are useful as photopolymerizable compositions.

Saam, in U.S. Pat. No. 3,440,261, discloses a method for making silanes and siloxanes containing at least one silicon-bonded N'-acyl-N-(aminoalkyl)-aminohydrocarbyl radical (herein also partially acylated diamine radical). However, the compounds of Saam are still amine-substituted compounds and the method of Saam is incapable of providing a silane or siloxane having fully modified diamine radicals, i.e. N,N'-diacyl-N-(aminohydrocarbyl)-aminohydrocarbyl radicals (herein also, fully acylated diamine radicals) or monocarboxylic acid salts of partially acylated diamine radicals.

Morehouse, U.S. Pat. No. 2,929,829, teaches that organosilicon compounds containing an acylamino group which is attached to a silicon atom through a polymethylene linkage that contains at least three carbon atoms can be prepared by the reaction of an organosilicon atom bearing an aminoalkylsilyl grouping with a monocarboxylic acid, or an ester, halide or anhydride thereof. Although the compounds of Morehouse are fully modified, full modification such as full acylation of diamine radical-containing organosilicon compounds, and the benefits attendant therewith, are not suggested.

Thus, while the art teaches reacting a silane or siloxane containing diamine radicals with various reactants to provide fully or partially derivatized diamine radicals, said fully or partially derivatized diamine radicals are still reactive, for example by way of residual amine radicals or by way of introduced reactive radicals, such as urea radicals, carboxyl radicals, etc. An improved method for modifying the reactivity of an organopolysiloxane which bears diamino radicals is therefore needed so that an even lower degree of amine reactivity is provided therefor without the introduction of other reactivities.

BRIEF SUMMARY OF THE INVENTION

It is an object of this invention to provide organopolysiloxane compounds that contain one or more fully modified silicon-bonded diamine radicals. It is a particular object of the present invention to provide fully modified diamine organopolysiloxane compounds. It is also an object of this invention to provide a process for preparing the compounds of this invention.

These objects, and others which may become apparent upon consideration of the following disclosure and appended claims, are obtained by treating an organopolysiloxane which contains at least one silicon-bonded diamine radical, i.e. N-(aminohydrocarbyl)-aminohydrocarbyl radical, having the formula ZHNQ'NHQ— or at least one partially acylated diamine radical, i.e. N'-acyl-N-(aminohydrocarbyl)-aminohydrocarbyl radical, having the formula ZANQ'NHQ—, with a monocarboxylic acid anhydride. The type of modification that results in the product of this process is dependent on the relative amounts of reactants and the reaction conditions that are used.

The above-summarized process and resultant compounds of this invention will now be described and exemplified in detail and particularly claimed by the appended claims.

DETAILED DESCRIPTION OF THE INVENTION

In one aspect, the present invention relates to an organopolysiloxane compound containing at least one siloxane unit selected from siloxane units having the formulae

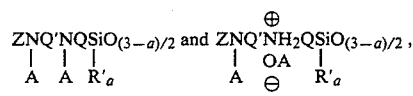

all other siloxane units in the organopolysiloxane compound being selected from siloxane units having the formulae

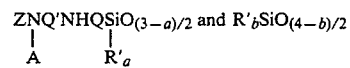

wherein, at each occurrence, Z denotes H or R'', R'' denotes a monovalent hydrocarbon radical, R' denotes a monovalent radical selected from hydrocarbon radicals, halogenated hydrocarbon radicals, hydrogen atoms, —OR'' radicals, —OH radicals and —OA radicals, Q and Q' each denote a divalent hydrocarbon radical, A denotes an acyl radical having the formula

R denotes a monovalent hydrocarbon radical or a halogenated monovalent hydrocarbon radical, a has a value of 0, 1 or 2 and b has a value of 0, 1, 2 or 3.

The compounds of this invention consist of a plurality of siloxane units, selected from the four types of siloxane units noted above, joined together by one or more silicon-oxygen-silicon bonds. The compounds of this invention can consist of any combination of two or more of said siloxane units provided that at least one siloxane unit thereof is a fully modified diamine siloxane unit, i.e. a siloxane unit having the formula

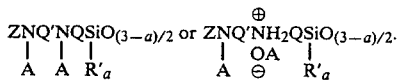

Thus, the compounds of this invention can consist solely of said fully modified diamine siloxane units or siloxane combinations thereof with partially acylated diamine siloxane units, i.e. siloxane units having the formula

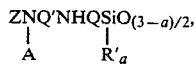

and/or other siloxane units, i.e. siloxane units having the formula $R'_bSiO_{(4-b)/2}$.

It is to be understood that since the present invention relates generally to a process which comprises, in one aspect, acylating a diamine-containing organopolysiloxane compound with a monocarboxylic acid anhydride and to the acylamino-containing organopolysiloxane compounds that are obtained therefrom, there exists the possibility of obtaining different acylamino structures when less than full acylation is attempted. That is to say, when a diamine-containing siloxane unit ZHNQ'NHQSi≡ is partially acylated, yet fully modified, the product is said to be an amine acylate salt having the formula

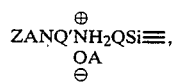

based on spectroscopic evidence, although there may be present a lesser portion of the isomeric

Likewise, although ZANQ'NHQSi≡ is said to be the predominate partially acylated siloxane unit, the presence of lesser amounts of ZHNQ'NAQSi≡ is not precluded thereby.

In the compounds of this invention Z denotes a hydrogen atom or an R'' radical where R'' denotes any monovalent hydrocarbon radical; such as an alkyl radical, such as methyl, ethyl, butyl, hexyl or octyl; a cycloaliphatic radical, such as cyclohexyl; an aryl or octyl radical, such as phenyl, benzyl, styryl, tolyl or xenyl; and an alkenyl radical, such as vinyl or allyl.

Herein, Q' and Q each denotes any divalent hydrocarbon radical such as an alkylene radical; such as —CH₂CH₂—,

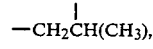

—CH₂CH₂CH₂—, —CH₂CH(CH₃)CH₂—, and —(CH₂)₆—; an arylene radical such as —C₆H₄—; or an aralkylene radical such as —CH₂C₆H₄— or —CH₂C₆H₄CH₂—.

In a preferred embodiment of this invention the compounds of this invention are prepared from amine-containing siloxane precursors that have been prepared from ethylene diamine and a suitable silicon compound and thus contain silicon bonded H₂NCH₂CH₂NHQ— radicals. Therefore, in the compounds of this invention Z preferably denotes the hydrogen atom and Q' preferably denotes the —CH₂CH₂— radical.

Q can be the same as, or different from, Q' in the compounds of this invention. Preferably Q is any alkylene radical containing 3 to 10 carbon atoms and there are at least three carbon atoms between the silicon atom and the nitrogen atom bonded to the Q radical. An example of a preferred Q radical has the formula —CH₂CH(CH₃)CH₂—.

The compounds of the present invention therefore most preferably contain

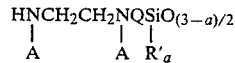

siloxane units, such as

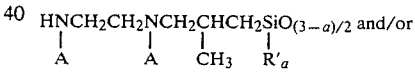

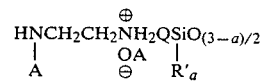

siloxane units, such as

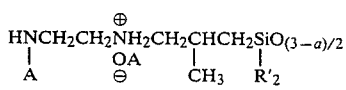

and, optionally,

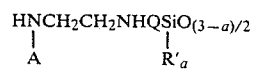

siloxane units, such as

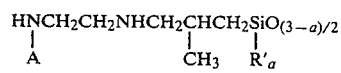

and/or $R'_bSiO_{(4-b)/2}$ siloxane units.

The siloxane units in the organopolysiloxane compounds of this invention can contain from zero to two silicon-bonded R' radicals (a equals 0, 1 or 2) on the fully modified or partially acylated diamine siloxane units and from zero to three silicon-bonded R' radicals (b equals 0, 1, 2 or 3) on said other siloxane units.

In the compounds of this invention each R' denotes any monovalent radical selected from the group consisting of hydrocarbon radicals, such as those denoted above for R''; halogenated hydrocarbon radicals such as 3,3,3-trifluoropropyl, chloropropyl, chloroisobutyl, and halophenyl; hydrogen atoms; OR'' radicals such as —OCH$_3$, —OCH$_2$CH$_3$ and —OCH(CH$_3$)$_2$; —OH radicals; and —OA radicals, such as —OCOCH$_3$ and —O-COC$_6$H$_5$. Preferably each R' contains no more than 6 carbon atoms. Most preferably R' denotes a methyl radical.

In the compounds of this invention each A denotes any acyl radical having the formula $$\underset{RC=O}{|}$$

wherein R denotes any monovalent hydrocarbon radical, such as those denoted above for R'', and halogenated forms thereof. Preferably the size of R is limited to from 1 to 6 carbon atoms to facilitate the preparation of the compounds of this invention and/or the removal of by-produced RCOOH therefrom, as delineated below. Most preferably A denotes $$\underset{CH_3C=O}{|}.$$

Examples of preferred fully acylated diamine siloxane units for the compounds of this invention include, but are not limited to, HNCH$_2$CH$_2$NCH$_2$CHCH$_2$SiO$_{3/2}$,
| | |
CH$_3$C=O   CH$_3$
       O=CCH$_3$ HNCH$_2$CH$_2$NCH$_2$CH$_2$CH$_2$SiO$_{3/2}$,
| |
CH$_3$C=O
       O=CCH$_3$ HNCH$_2$CH$_2$NCH$_2$CHCH$_2$SiO$_{2/2}$,
| | | |
CH$_3$C=O   CH$_3$   CH$_3$
       O=CCH$_3$ HNCH$_2$CH$_2$NCH$_2$CH$_2$CH$_2$SiO$_{2/2}$,
| | |
CH$_3$C=O   CH$_3$
       O=CCH$_3$ CH$_3$
                        |
HNCH$_2$CH$_2$NCHCHCH$_2$SiO$_{1/2}$ and
| | | |
CH$_3$C=O   CH$_3$   CH$_3$
       O=CCH$_3$ CH$_3$
                             |
HNCH$_2$CH$_2$NCH$_2$CH$_2$CH$_2$SiO$_{1/2}$.
| | |
CH$_3$C=O     CH$_3$
       O=CCH$_3$ Examples of preferred partially acylated diamine siloxane units for the compounds of this invention include, but are not limited to, HNCH$_2$CH$_2$NHCH$_2$CHCH$_2$SiO$_{2/2}$ and
| | |
CH$_3$C=O   CH$_3$   CH$_3$ HNCH$_2$CH$_2$NHCH$_2$CH$_2$CH$_2$SiO$_{2/2}$
| |
CH$_3$C=O             CH$_3$ and the corresponding analogs bearing one less or one more methyl group bonded to the silicon atom, i.e. a=0 or 2, respectively.

Examples of preferred fully modified diamine siloxane units, other than fully acylated diamine siloxane units, for the compounds of this invention include, but are not limited to, ⊕
HNCH$_2$CH$_2$NH$_2$CH$_2$CHCH$_2$SiO$_{2/2}$ and
|          O$_2$CCH$_3$ |   |
CH$_3$C=O    ⊖      CH$_3$   CH$_3$ ⊕
HNCH$_2$CH$_2$NH$_2$CH$_2$CH$_2$CH$_2$SiO$_{2/2}$
|          O$_2$CCH$_3$     |
CH$_3$C=O    ⊖            CH$_3$ and the corresponding analogs bearing one less or one more methyl group bonded to the silicon atom.

Examples of suitable other siloxane units for the compounds of this invention include, but are not limited to, where Me denotes the methyl radical, Et denotes the ethyl radical, Vi denotes the vinyl radical and Ph denotes the phenyl radical, Me$_3$SiO$_{\frac{1}{2}}$, Me$_2$ViSiO$_{\frac{1}{2}}$, PhMeViSiO$_{\frac{1}{2}}$, Me$_2$SiO$_{2/2}$, MeViSiO$_{2/2}$, MePhSiO$_{2/2}$, MeEtSiO$_{2/2}$, Ph$_2$SiO$_{2/2}$, MeSiO$_{3/2}$, PhSiO$_{3/2}$, ViSiO$_{3/2}$, EtSiO$_{3/2}$, SiO$_{4/2}$, Me$_2$(HO)SiO$_{\frac{1}{2}}$, Me$_2$(CH$_3$O)SiO$_{\frac{1}{2}}$, Me(OH)SiO$_{2/2}$, Me(OCH$_3$)SiO$_{2/2}$, Me$_2$(CH$_3$CO$_2$)SiO$_{\frac{1}{2}}$ and Me(H)SiO$_{2/2}$. Preferably said other siloxane units in the compounds of this invention are methylsiloxane units, such as Me$_3$SiO$_{\frac{1}{2}}$, Me$_2$SiO$_{2/2}$ and MeSiO$_{3/2}$ siloxane units.

In accordance with one of the objects of this invention the preferred organopolysiloxane compounds of this invention are substantially free of partially acylated diamine siloxane units. That is to say, the organopolysiloxane compounds of the present invention preferably consist of fully modified diamine siloxane units having the formulae ⊕
ZNQ'NQSiO$_{(3-a)/2}$ and/or ZNQ'NH$_2$QSiO$_{(3-a)/2}$
| |  |                      |   OA   |
A A R'$_a$                   A   ⊖    R'$_a$ and combinations thereof with other siloxane units having the formula R'$_b$SiO$_{(4-b)/2}$, each delineated above.

Organopolysiloxane compounds of this invention which consist of two or more fully modified diamine siloxane units are homopolymers because they are free of copolymerized R'$_b$SiO$_{(4-b)/2}$ and all siloxane units in the organopolysiloxane have the formulae ⊕
ZNQ'NQSiO$_{(3-a)/2}$ and/or ZNQ'NH$_2$QSiO$_{(3-a)/2}$.
| |  |                      |   OA   |
A A R'$_a$                   A   ⊖    R'$_a$ The homopolymeric organopolysiloxane compounds of this invention can have any polysiloxane molecular structure such as a cyclic polysiloxane, a linear polysiloxane and a branched polysiloxane structure.

Commensurate with the above-described preferred identities of Z, Q', Q and R' a preferred organopolysiloxane homopolymer compound of this invention is a fully acylated organopolysiloxane consisting of

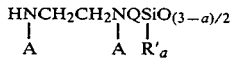

A most preferred fully acylated homopolymeric compound of this invention is a mixture of linear and cyclic polysiloxanes having the average formula

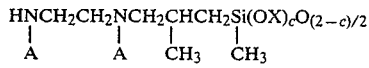

wherein c has an average value of from 0 to 1 and X denotes H, R" or A. It is to be understood that when c has a value of greater than zero, the indicated OX radicals can be present as any combination of —OH, —OR" and —OA radicals.

Organopolysiloxane compounds of this invention which consist of one or more fully modified diamine siloxane units having the formula

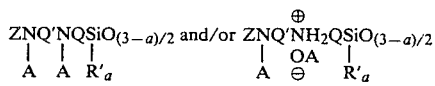

and one or more other siloxane units having the formula $R'_bSiO_{(4-b)/2}$ are copolymers and, like the homopolymers of this invention described above, can have any polysiloxane molecular structure, such as a cyclic copolysiloxane, a linear copolysiloxane and a branched copolysiloxane structure.

Commensurate with the above-described preferred identities of Z, Q', Q and R' a preferred organopolysiloxane copolymer compound of this invention is a fully acylated organopolysiloxane consisting of at least one siloxane unit having the formula

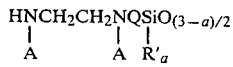

and at least one siloxane unit having the formula $R'_bSiO_{(4-b)/2}$. As with the homopolymer organopolysiloxane compounds of this invention the copolymer organopolysiloxanes of this invention can contain silicon-bonded —OX radicals, i.e. OH radicals and/or hydrolyzable precursors thereto, such as silicon-bonded —OR" and —OA radicals, depending upon how the organopolysiloxane compounds were prepared. For example, when the organopolysiloxane compound of this invention are prepared by the method of this invention, delineated below, silicon-bonded —OH radicals and —OR" radicals may be converted to silicon-bonded —OA radicals. These —OA radicals may be subsequently hydrolyzed, partially or completely, to silicon-bonded —OH radicals by the action of adventitious water.

A preferred fully acylated copolymeric organopolysiloxane compound of this invention has the general formula

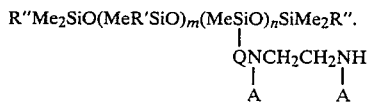

A highly preferred fully acylated copolymeric organopolysiloxane compound of this invention is a linear copolysiloxane having the formula

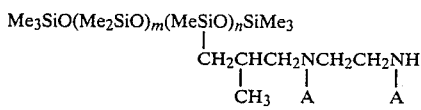

Herein m and n have an average value of from 0 to 10,000 and from 1 to 10,000, respectively. A particular example of a highly preferred linear copolymer of the present invention has the fully acylated copolymeric formulae noted above and contains from 1 to about 5 mol percent of the fully acylated diamine siloxane units. That is to say, n has a value of at least one but, for values of m equal to or greater than 20, not greater than 0.05 m. For example, in this highly preferred embodiment the average values of m and n can be, respectively, 0 and 1, 1 and 1, 4 and 1, 10 and 1, 50 and 1, 75 and 1, 75 and 1.5, 90 and 2, 200 and 1, 200 and 4, 1000 and 1, 1000 and 2, 1000 and 7.2 and 1000 and 50.

Another example of a preferred fully modified organopolysiloxane copolymer compound of this invention has the general formula

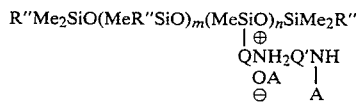

wherein each R" typically denotes a methyl radical and the general and preferred values of m and n therein are as disclosed above.

In particular, valuable organopolysiloxane compounds of this invention having the above copolymeric formulae are obtained when n has an average value of from 1 to about 0.05 m, A denotes

and m has a value of from 0 to about 1000, preferably from 50 to about 500. These compounds possess the well-known desirable features of polydimethylsiloxanes, such as slipperiness, and thermal stability and the features of acylamine compounds, such as polarity. Furthermore, these compounds are more easily prepared by the process of this invention delineated below, and more easily handled than compounds of this invention which contain larger amounts of acylated diamine siloxane units.

The organopolysiloxane compounds of this invention can be prepared by the process of this invention which generally stated, comprises mixing a suitably constituted amine-containing organopolysiloxane compound and a monocarboxylic acid anhydride in certain amounts and under certain reaction conditions so that amine-containing siloxane units are modified, at least one fully.

More specifically, another aspect of the present invention relates to a process for preparing an organopolysiloxane compound containing at least one siloxane unit selected from siloxane units having the formulae $$ZNQ'NQSiO_{(3-a)/2} \text{ and } ZNQ'\overset{\oplus}{N}H_2QSiO_{(3-a)/2},$$
$$\underset{A}{|}\ \underset{A}{|}\ \underset{R'_a}{|} \quad\quad \underset{A}{|}\ \underset{\ominus}{OA}\ \underset{R'_a}{|}$$

all other siloxane units in the organopolysiloxane compound being selected from siloxane units having the formulae $$ZNQ'NQSiO_{(3-a)/2} \text{ and } R'_bSiO_{(4-b)/2},$$
$$\underset{A}{|}\ \underset{H}{|}\ \underset{R'_a}{|}$$

said process comprising:

(I) mixing components comprising:

(i) an amine-containing organopolysiloxane compound containing at least one siloxane unit having the formula $$ZNQ'NQSiO_{(3-a)/2},$$
$$\underset{Y}{|}\ \underset{H}{|}\ \underset{R'_a}{|}$$

all other siloxane units in the amine-containing organopolysiloxane compound having the formula $R'_bSiO_{(4-a)/2}$ and (ii) a monocarboxylic acid anhydride having the formula $A_2O$, the amounts of component (i) and component (ii) being sufficient to provide at least one mol of component (ii) for every mol of component (i) and for every siloxane unit, exceeding one having the formula $$ZNQ'NQSiO_{(3-a)/2}$$
$$\underset{H}{|}\ \underset{H}{|}\ \underset{R'_a}{|}$$

in the average molecule of component (i); wherein, at each occurrence, Z denotes H or R", R" denotes a monovalent hydrocarbon radical, R' denotes a monovalent radical selected from hydrocarbon radicals, halogenated hydrocarbon radicals, hydrogen atoms, —OR" radicals, —OH radicals and —OA radicals, Q and Q' each denote a divalent hydrocarbon radical, A denotes an acyl radical having the formula $$\underset{RC=O}{|},$$

R denotes a monovalent hydrocarbon radical or a halogenated monovalent hydrocarbon radical, Y denotes H or A, a has a value of 0, 1 or 2 and b has a value of 0, 1, 2 or 3 and (II) maintaining the mixture of (I) at a temperature of from 0° C. to 300° C. for a length of time sufficient for the formation of at least one siloxane unit selected from siloxane units having the formulae $$ZNQ'NQSiO_{(3-a)/2} \text{ and } ZNQ'\overset{\oplus}{N}H_2QSiO_{(3-a)/2}.$$
$$\underset{A}{|}\ \underset{A}{|}\ \underset{R'_a}{|} \quad\quad \underset{A}{|}\ \underset{\ominus}{OA}\ \underset{R'_a}{|}$$

In the components (i) and (ii) that are used in the process of this invention the general and preferred meanings for Z, Q', Q, a, b, R", R', R and A are as delineated above for the organopolysiloxane compounds of this invention. Also, the general and preferred organopolysiloxane compounds of this invention, and their general and preferred siloxane units, which are delineated above are the general and preferred products of the process of this invention.

In addition, in component (i) of the process of this invention Y denotes a hydrogen atom or an acyl radical, A, having, as indicated above, the formula $$\underset{RC=O}{|}$$

wherein R preferably contains from 1 to 6 carbon atoms, and most preferably 1 carbon atom.

The amine-containing organopolysiloxane component (i) contains a plurality of siloxane units, at least one of which is an amine-containing siloxane unit having the formula $$ZNQ'NQSiO_{(3-a)/2}.$$
$$\underset{Y}{|}\ \underset{H}{|}\ \underset{R'_a}{|}$$

In the process of this invention substantially all of any diamine siloxane units (Y=H) are converted to the corresponding partially acylated diamine siloxane units (Y=A). In addition, from one to substantially all partially acylated diamine siloxane units (Y=A) are further modified to fully modified diamine siloxane units, as defined above.

The amine-containing organopolysiloxane component (i) can have any polysiloxane molecular structure such as a cyclic polysiloxane, a linear polysiloxane and a branched polysiloxane structure and can further be a homopolymer of amine-containing siloxane units or a copolymer of amine-containing siloxane units and other siloxane units, noted above.

The amine-containing organopolysiloxane component (i) can contain one or more types of said amine-containing siloxane units. For example, component (i) can contain $$H_2NQ'NHQSiO_{(3-a)/2}$$
$$\underset{R'_a}{|}$$

units or $$HNQ'NHQSiO_{(3-a)/2}$$
$$\underset{A}{|}\quad \underset{R'_a}{|}$$

units. Alternatively, component (i) can contain both $$HNQ'NHQSiO_{(3-a)/2}$$
$$\underset{A}{|}\quad \underset{R'_a}{|}$$

units and $$H_2NQ'NHQSiO_{(3-a)/2}.$$
$$\underset{R'_a}{|}$$

Furthermore component (i) can contain $$R''NHQ'NHQSiO_{(3-a)/2}$$
$$|$$
$$R'_a$$

units and/or $$R''NQ'NHQSiO_{(3-a)/2}$$
$$|\quad\quad|$$
$$A\quad\quad R'_a$$

units with or without one or more of the diamine siloxane units delineated immediately above. Component (i), in any case, can further comprise one or more $R'_bSiO_{(4-b)/2}$ siloxane units.

For amine-containing units of component (i) wherein Y denotes A, proper delineation thereof can be found above in the description of organopolysiloxane compounds of this invention comprising partially acylated diamine siloxane units.

Amine-containing siloxane units of component (i) wherein Y denotes H are diamine siloxane units having the formula $$ZNQ'NQSiO_{(3-a)/2}$$
$$|\ \ |\ \ |$$
$$H\ \ H\ \ R'_a$$

wherein Z, Q', Q, R' and a have the general and preferred meanings delineated above. In particular, the present invention, in all its aspects, preferably relates to compounds based on ethylene diamine, thereby giving rise to preferred diamine siloxane units having the formula $$H_2NCH_2CH_2NHQSiO_{(3-a)/2}.$$
$$|$$
$$R'_a$$

Examples of preferred diamine siloxane units in component (i) include, but are not limited to, $$H_2NCH_2CH_2NHCH_2CH_2CH_2SiO_{3/2},$$

$$H_2NCH_2CH_2NHCH_2CHCH_2SiO_{3/2},$$
$$|$$
$$CH_3$$

$$H_2NCH_2CH_2NHCH_2CH_2CH_2SiO_{2/2},$$
$$|$$
$$CH_3$$

$$H_2NCH_2CH_2NHCH_2CHCH_2SiO_{2/2},$$
$$|\quad\quad|$$
$$CH_3\ \ CH_3$$

$$\quad\quad\quad\quad\quad\quad CH_3$$
$$\quad\quad\quad\quad\quad\quad |$$
$$H_2NCH_2CH_2NHCH_2CH_2CH_2SiO_{1/2}\text{ and}$$
$$\quad\quad\quad\quad\quad\quad |$$
$$\quad\quad\quad\quad\quad\quad CH_3$$

$$\quad\quad\quad\quad\quad\quad\quad CH_3$$
$$\quad\quad\quad\quad\quad\quad\quad |$$
$$H_2NCH_2CH_2NHCH_2CHCH_2SiO_{1/2}.$$
$$\quad\quad\quad\quad\quad\quad |\quad\ \ |$$
$$\quad\quad\quad\quad\quad\quad CH_3\ \ CH_3$$

Examples of other siloxane units in component (i) having the formula $R'_bSiO_{(4-b)/2}$ are the same as those general and preferred units of the same formula delineated above for the organopolysiloxane compounds of this invention.

Amine-containing organopolysiloxane compounds that are useful in the process of this invention are well known in the organosilicon art. The disclosures of U.S. Pat. Nos. 3,355,424; 2,971,864; 3,046,295; 4,336,395; 3,146,250 and 3,440,261 are incorporated herein to teach how to make said component (i).

In the process of this invention component (i) is preferably an amine-containing organopolysiloxane wherein the amine-containing siloxane units thereof are solely ethylene diamine siloxane units (Y=Z=H), there being substantially no partially acylated diamine siloxane units (Y=A) therein. That is to say, component (i) to be acylated in the process of this invention preferably consists of siloxane units having the formula $$H_2NCH_2CH_2NHQSiO_{(3-a)/2}$$
$$|$$
$$R'_a$$

and, optionally, siloxane units having the formula $R'_bSiO_{(4-b)/2}$.

Most preferably component (i) in the process of this invention is a linear compound having the formula $$Me_3Si(Me_2SiO)_m(MeSiO)_nSiMe_3$$
$$|$$
$$CH_2CHCH_2NHCH_2CH_2NH_2$$
$$|$$
$$CH_3$$

wherein Me, m and n are as generally and preferably denoted above.

Component (ii) that is mixed with component (i) in the process of this invention is any monocarboxylic acid anhydride having the formula $A_2O$ wherein A denotes $$|$$
$$RC=O$$

and R has the general and preferred meanings delineated above. As noted above component (ii) preferably contains from 1 to 6 carbon atoms in each R radical to facilitate the preparation of the compounds of this invention and/or the removal of any by-produced RCOOH therefrom. Acetic anhydride is a preferred component (ii) because it is highly reactive with amine-containing organopolysiloxanes, it and its by-product acetic acid are readily removable by distillation from the organopolysiloxane product of the process of this invention, it is economically available and its by-product acetic acid is physiologically acceptable.

In the process of this invention components comprising said amine-containing organopolysiloxane component (i) and said monocarboxylic acid anhydride component (ii), and any non-essential components such as a reaction diluent or catalyst, are mixed, preferably under anhydrous conditions and at room temperature. If necessary, the resulting mixture can be heated to a temperature of up to 300° C. to aid the process; however, initial cooling of the mixture, e.g. to 0° C., is sometimes needed. The reaction mixture, whether heated or not, is maintained until the herein delineated desired degree of acylation of component (i) has occurred, after which any unreacted $A_2O$ and/or AOH is preferably removed from the reaction mixture.

Typically components (i) and (ii) are mixed and, after any initial exotherm has ceased, heated at 50° to 150° C. for a period of up to an hour or more. The extent of reaction can be determined by spectroscopic means, such as infrared and/or nuclear magnetic resonance spectroscopy, and/or gravimetric or volumetric means, such as amine neutral equivalent, detailed below.

The amounts of components (i) and (ii) that are mixed in the process of this invention are merely those amounts that will convert every diamine siloxane unit in component (i) to a partially acylated diamine siloxane unit and at least one of the latter siloxane units to a fully modified diamine siloxane unit.

The minimum amount of monocarboxylic acid anhydride needed to react with an organopolysiloxane component (i) wherein the only amine-containing siloxane units have the formula

is one mol of $A_2O$ for every mol of amine-containing organopolysiloxane compound. One molecular portion of anhydride will convert an average of one partially acylated diamine siloxane unit per one molecular portion of component (i) to a fully acylated diamine siloxane unit, thereby providing a compound of this invention.

The minimum amount of monocarboxylic acid anhydride needed to react with an organopolysiloxane component (i) wherein the only amine-containing siloxane units have the formula

is one mol of $A_2O$ for every diamine siloxane unit in the amine-containing organopolysiloxane. In this case the diamine siloxane units are converted to partially acylated diamine siloxane units which react further with monocarboxylic acid to produce the carboxylic acid salt of the partially acylated diamine siloxane units having the formula

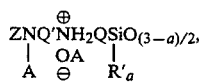

thereby providing a compound of this invention.

Thus, the minimum amount of component (ii) that is mixed with component (i) in the process of this invention is that amount that will provide one mol of $A_2O$ for every mol of component (i) plus one mol of $A_2O$ for every siloxane unit, exceeding one, in the average molecule of component (i) that has the formula

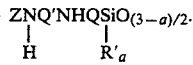

There is no known upper limit to the amount of component (ii) per unit amount of component (i) that can be used in the process of this invention; however, the use of amounts in substantial excess of one mol of component (ii) for every amine nitrogen atom in component (i) are not required to provide the fully acylated compositions of this invention and is therefore not desired.

In a preferred embodiment of the present invention the preferred component (i) noted above consisting of amine-containing siloxane units having the formula

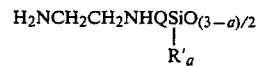

and, optionally, other siloxane units having the formula $R'_bSiO_{(4-b)/2}$ is mixed with substantially one mol of $A_2O$ for every amine-containing siloxane unit in the average formula for component (i). In this aspect of the present invention substantially every amine-containing siloxane unit is fully modified to a siloxane unit having the formula

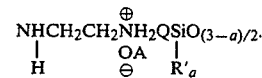

The resulting fully modified organopolysiloxane compound of this invention can be used without further purification because it is substantially free of monocarboxylic acid anhydride and monocarboxylic acid.

Alternatively, said resulting fully modified organopolysiloxane compound of this invention can be subjected to a distillation process, preferably at elevated temperatures such as from 120° C. to 300° C., preferably 150° C. to 250° C., and most preferably about 200° C., whereupon the amine salt radicals are changed and volatile material such as monocarboxylic acid (AOH), water, cyclic polysiloxanes and disiloxanes, are distilled. There remains a residue comprising an organopolysiloxane compound comprising siloxane units having the formulae

and, unexpectedly,

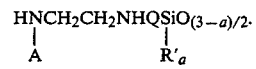

For this aspect of the invention component (ii) is preferably a volatile anhydride such as acetic anhydride.

In another preferred embodiment of the present invention the preferred component (i) noted above consisting of amine-containing siloxane units have the formula

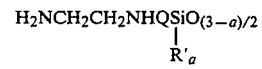

and, optionally, other siloxane units having the formula $R'_bSiO_{(4-b)/2}$ is mixed with at least two mols of $A_2O$ for every amine-containing siloxane unit in the average formula for component (i). In this aspect of the present invention substantially every amine-containing siloxane unit is fully acylated to a siloxane unit having the formula

The resulting fully acylated organopolysiloxane compound of this invention can be used without further purification; however, it is preferably further purified by removing at least the monocarboxylic acid (AOH) that was formed during the reaction and any unreacted component (ii). Said acid and any unreacted component (ii) can be removed by any suitable method such as by extraction, absorption, filtration, decomposition, distillation, decantation, neutralization and derivitization or combinations thereof. When possible, without resorting to extreme temperatures, a process comprising distillation is preferably used to remove any anhydride reactant and/or corresponding acid. When a process comprising distillation is used component (ii) is preferably a volatile anhydride, such as acetic anhydride.

The incompletely acylated compounds of this invention are useful as reactive components by virtue of residual

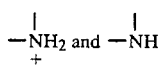

groups. The completely acylated compounds of this invention are useful as surface active agents, lubricants, etc. by virtue of their polarity and relative chemical inertness. Compounds of this invention bearing reactive silicon-bonded radicals, such as H, vinyl, alkoxy, acetoxy and hydroxy can be converted to the gelled or cured state by well-known methods to confer useful mechanical properties thereto.

The following examples are disclosed by way of illustrating, but not limiting, the present invention, which is properly delineated by the appended claims.

Amine neutral equivalent (A.N.E.) denotes the parts by weight of a material that is required to provide 14.007 parts by weight of amine and/or amine salt nitrogen. It was determined by dissolving the sample in a mixture of toluene and glacial acetic acid and titrating the solution anhydrously with perchloric acid to a methyl violet endpoint.

All parts and percentages herein are by weight, unless otherwise stated. Viscosities were determined at room temperature, using a rotating spindle viscometer.

EXAMPLE 1

A mixture of 5.60 parts (0.025 mols) of Me(OMe)$_2$SiCH$_2$CH(CH$_3$)CH$_2$NHCH$_2$CH$_2$NH$_2$, 2.04 parts (0.025 mols) of Me$_3$SiO$_{\frac{1}{2}}$ siloxane units, 91.86 parts (1.24 mols) of Me$_2$SiO$_{2/2}$ siloxane units and 0.60 parts of aqueous KOH was heated at 150° C. for 4 hours to hydrolyze the silicon-methoxy bonds, to remove the methanol and water and to equilibrate the siloxane units. The product was cooled, treated with NaHCO$_3$ and filter aid and filtered to produce a fluid having a viscosity of 150 centipoise, a specific gravity of 0.97 and an A.N.E. of about 2000. The product was a mixture of 10% cyclopolydimethylsiloxanes and 90% of an organopolysiloxane having the nominal formula

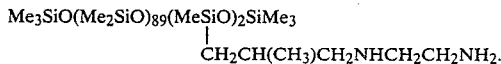

A 1-liter, 3-necked flask fitted with a stirring paddle, thermometer and fractional distilling head was charged with 700.0 g of the above-described mixture of cyclopolydimethylsiloxanes and organopolysiloxane. Excess acetic anhydride, 45.0 g (0.440 mols; mols anhydride/diamine=2.4) was added rapidly to the stirred organopolysiloxane mixture which caused the temperature of the mixture to rise from 21° C. to 49° C. The reaction mixture was then heated to 190° C. for 3.5 hours, allowing volatile material to distill. The reaction product was further freed of volatile material by heating the reaction mixture to 150° C. at a pressure of 1 Torr. The non-volatile product was cooled, filtered and analyzed by infrared spectroscopy. The infrared spectrum showed —NH stretching for

at 3340 to 3330 cm$^{-1}$; carbonyl stretching for

at 1680 cm$^{-1}$ and for

at 1640 to 1635 cm$^{-1}$. The infrared spectrum of the starting organopolysiloxane containing amine radicals was free of absorption bands at the above-listed frequencies. The infrared spectra of starting organopolysiloxane and final organopolysiloxane also showed the usual absorption bonds at 1110 to 1010 cm$^{-1}$ for siloxane linkages. The product was an organopolysiloxane having the nominal formula

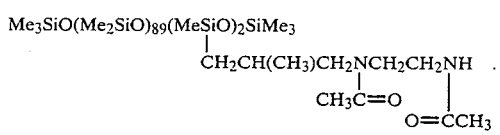

When this reaction was repeated, using 8% excess of acetic anhydride instead of 20% excess, and the product was freed of volatile material with a wiped-film stripper, a product having an A.N.E.=53,246 was obtained. Approximately 96% of the amine radicals had been acylated.

The product of this reaction was useful as a mold-release component in a molded polymeric composition, decreasing the mold-release force by 54%. The starting organopolysiloxane mixture containing diamine-containing siloxane units was ineffective in reducing the mold-release force of the molded polymeric composition.

EXAMPLE 2

An organopolysiloxane mixture identical to that used in Example 1 was freed of the cyclopolydimethylsiloxane portion by vacuum distillation at reduced pressure. The resulting organopolysiloxane had an amine neutral equivalent of 1784 and the formula $$\text{Me}_3\text{SiO}(\text{Me}_2\text{SiO})_{89}(\text{MeSiO})_2\text{SiMe}_3$$
$$|$$
$$\text{CH}_2\text{CH}(\text{CH}_3)\text{CH}_2\text{NHCH}_2\text{CH}_2\text{NH}_2.$$

One hundred parts of this organopolysiloxane (0.056 eq. of amine) was rapidly treated with 2.86 parts of acetic anhydride (mols anhydride/diamine=1.0) as in Example 1. The resulting product had an amine neutral equivalent of 3541, indicating that 50% of the amine had been acylated. The product was then heated at 102° C. for one hour and was found to have an A.N.E.=3856, indicating that 54% of the amine radicals had been acylated. Infrared spectroscopy showed absorption at 1610 to 1600 cm$^{-1}$ for amide carbonyl and at 1570 cm$^{-1}$ for acetate ion. The product had the formula $$\text{Me}_3\text{SiO}(\text{Me}_2\text{SiO})_{89}(\text{MeSiO})_2\text{SiMe}_3 \qquad \text{O}$$
$$| \qquad\qquad\qquad\qquad\qquad\quad \oplus \qquad\qquad ||$$
$$\text{CH}_2\text{CH}(\text{CH}_3)\text{CH}_2\text{NH}_2\text{CH}_2\text{CH}_2\text{NHCCH}_3.$$
$$\text{CH}_3\text{CO}_2^{\ominus}$$

EXAMPLE 3

An organopolysiloxane mixture identical to that used in Example 1 was rapidly treated with acetic anhydride (mols anhydride/diamine=1.1) at 30° C. and the resulting product was then heated at 150° C. for 2 hours. Volatile products were then distilled from the reactive mixture at 150° C. and 10 Torr. The light yellow-colored fluid had a viscosity of 311 cs., an A.N.E.=4896 (indicating that about 61% of the amine radicals had been acylated) and infrared absorption for amide carbonyl at 1680 cm$^{-1}$ $$|$$
$$(-\text{CONH})$$

and at 1650 to 1620 cm$^{-1}$ $$| \qquad\qquad |$$
$$(-\text{CONH, amide II and }-\text{CON}-\text{, amide I}).$$

Integration of the H$^1$ nuclear magnetic resonance spectrum in the region of the $$\text{N}$$
$$|$$
$$\text{CH}_3\text{C}=\text{O}$$

signal indicated that the ratio of $$-\text{NH}$$
$$|$$
$$\text{CH}_3\text{C}=\text{O}$$

($\delta$=2.0 ppm) radicals to $$-\text{N}-$$
$$|$$
$$\text{CH}_3\text{C}=\text{O}$$

($\delta$=2.2 ppm) radicals was about 3/1 indicating that about 67% of the amine radicals had been fully acylated.

The product was therefore a mixture of siloxanes having the average structure $$\text{Me}_3\text{SiO}(\text{Me}_2\text{SiO})_{89}(\text{MeSiO})_{0.7}(\text{MeSiO})_{1.3}\text{SiMe}_3$$
$$|\qquad\qquad |$$
$$\text{E}\qquad\quad \text{F}$$

where E denotes $$-\text{CH}_2\text{CHCH}_2\text{NHCH}_2\text{CH}_2\text{NH}$$
$$|\qquad\qquad\qquad\qquad |$$
$$\text{CH}_3 \qquad\qquad\qquad \text{CH}_3\text{C}=\text{O}$$

and F denotes $$-\text{CH}_2\text{CHCH}_2\text{NCH}_2\text{CH}_2\text{NH} \ .$$
$$|\qquad\quad |\qquad\quad\quad\quad\quad |$$
$$\text{CH}_3 \qquad \text{O}=\text{CCH}_3$$
$$\qquad\quad |$$
$$\qquad\text{CH}_3\text{C}=\text{O}$$

When the composition of this example was applied to tangled hair and the hair was combed, a 51% reduction of combing force was obtained.

EXAMPLE 4

An organopolysiloxane identical to that which was treated with acetic anhydride in Example 2 was treated with excess acetic anhydride (mols anhydride/diamine=2.4) in a nitrogen atmosphere over a period of 5 minutes. The resulting reaction mixture was then heated at 150° C. for 2 hours. The product had an A.N.E.=72,808, indicating that 97.5% of the amine radicals had been acylated. The product was then freed of volatile materials at 150° C. and 10 Torr, using a wiped film stripper. The A.N.E. of the volatile-free product was 89,127, indicated that 98% of the amine radicals had been acylated. The product has the formula $$\text{Me}_3\text{SiO}(\text{Me}_2\text{SiO})_{89}(\text{MeSiO})_2\text{SiMe}_3$$
$$|$$
$$\text{CH}_2\text{CH}(\text{CH}_3)\text{CH}_2\text{NCH}_2\text{CH}_2\text{NH} \ .$$
$$|\qquad\qquad\qquad |$$
$$\text{CH}_3\text{C}=\text{O}\quad\quad \text{CH}_3\text{C}=\text{O}$$

When this reaction was repeated, except that one mol of acetic anhydride for every amine radical was used (mols anhydride/diamine=2.0), a product having a A.N.E.=67,000 was obtained after the volatilization step.

EXAMPLE 5

The trisiloxane $$\text{Me}$$
$$|$$
$$\text{Me}_3\text{SiOSiOSiMe}_3$$
$$|$$
$$\text{CH}_2\text{CHCH}_2\text{Cl}$$
$$|$$
$$\text{CH}_3$$

(53 g) was slowly added to refluxing ethylene diamine (110 g). The reaction mixture was refluxed for 2 hours and then cooled to room temperature and the layers were separated. Vacuum distillation gave 45.7 g of

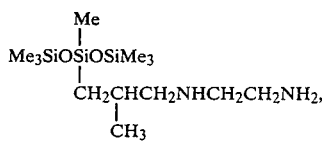

b.p. = 103°–105° C./3 Torr.

A 100 ml. flask was charged with 7.48 g (0.022 mols) of

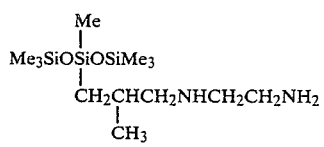

and 10 g of hexane and followed by 5.00 g (0.049 mols) of acetic anhydride (mols anhydride/diamine=2.2). After being heated at 69° C. for 1 hour the reaction mixture was washed repeatedly with aqueous NaHCO₃ (5%) until the washings were neutral and then with distilled water. The water-washed product was dried, freed of hexane at 60° C./25 mm pressure and the residue was analyzed by H' nuclear magnetic resonance spectroscopy. The spectrum showed substantially equal integrated signals for

($\delta$=2.0 ppm) radicals and

($\delta$=2.2 ppm) radicals. The product had the formula

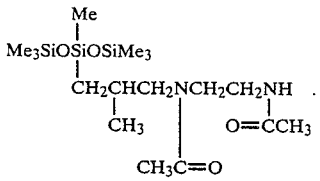

EXAMPLE 6

The acylation reaction of Example 5 was repeated except that pentane was used instead of hexane and the ration of mols of acetic anhydride to diamine radicals was 1.0 instead of 2.2. The product and the starting material were analyzed by H¹ nuclear magnetic resonance spectroscopy. Integration of the signals for

($\delta$=2.0 ppm) and

($\delta$=2.2 ppm) showed the product to be a 56/44 mixture of siloxanes having the formulae

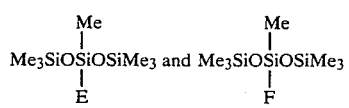

wherein E and F have the same meanings as noted in Example 3.

EXAMPLE 7

A mixture of 24.09 mols of Me₂SiO₂/₂ siloxane units, 0.44 mols of Me(OMe)₂-SiCH₂CH(CH₃)CH₂NHCH₂CH₂NH₂, 0.11 moles of Me₃SiO₁ siloxane units, 0.48 mols of water and 0.07 mols of KOH was heated at 150° C. for 2 hours under a N₂ sweep. Methanol and water were removed from the reaction mixture as they were formed. The resulting product was a mixture of cyclopolydimethylsiloxane and an organopolysiloxane having the formula

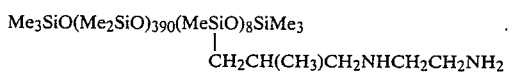

The mixture was cooled to 30° C. and treated with 10% excess acetic anhydride, 0.968 mols (mols anhydride/diamine=2.2). The reactive mixture was heated to 150° C. for 1 hour, cooled, filtered and then freed of volatile material at 150° C. and 25 Torr. The clear, yellow-colored fluid had a viscosity of 45,500 centipoise. Infrared and nuclear magnetic spectroscopy showed that all amine radicals had been acylated with CH₃CO₂— radicals. I.r: 3340 to 3330 cm⁻¹, amide NH stretch; 1680 cm⁻¹, carbonyl for

1640 to 1630 cm⁻¹, carbonyl for

EXAMPLE 8

An organopolysiloxane equilibrium mixture of Me₃SiO₁₇₈ siloxane units, Me₂SiO₂/₂ siloxane units and

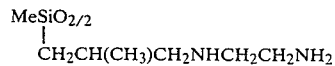

siloxane units having an A.N.E. of 1796 was treated with 10% excess benzoic anhydride (mols anhydride/diamine=2.2). The reaction mixture was heated to 150° C. for 2 hours and was freed of volatile material at 150° C. and 144 Torr. The residue was cooled and filtered to provide a fluid having a viscosity of 776 centipoise, an A.N.E. = 209,000 and containing a trace of benzoic acid. Infrared spectroscopy showed the presence of amide NH stretching at 3340 to 3330 cm$^{-1}$, carbonyl stretching at 1660 cm$^{-1}$ for

and at 1615 cm$^{-1}$ for

Nuclear magnetic resonance spectroscopy showed the disappearance of the —NH signal at 1.7δ that was present in the starting material. The product therefore was an equilibrium mixture of Me$_3$SiO$_\frac{1}{2}$, Me$_2$SiO$_{2/2}$ and

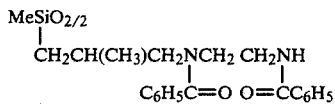

siloxane units.

EXAMPLE 9

Fifty grams (0.574 eq. of amine) of a cyclic and linear OX-endblocked organopolysiloxane having the repeating unit

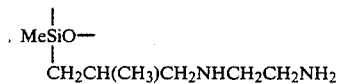

was treated with a 100% excess of acetic anhydride (117.4 g=1.149 mols) over a 45 minute period. The temperature of the reaction was controlled by immersing the reaction vessel in an ice bath. After being stirred for 30 minutes the reaction product was freed of volatile material at 100° C. and 3 Torr to yield a clear, red-colored thermoplastic solid.

The reaction was repeated except 19.3 g (0.189 mols) of acetic anhydride was placed in the flask and 15.0 g (0.086 mols) of the amine-containing organopolysiloxane was slowly added to the acetic anhydride. When about 5 g of the organopolysiloxane had been added 10.0 g of toluene was added to the flask to reduce the viscosity of the reaction mixture. When the addition of organopolysiloxane was completed the reactive mixture was heated for 110° C. for 50 minutes. The resulting product was devolitilized at 90° C. and 3 Torr and the devolitilized viscous fluid was further purified by dissolving it in CHCl$_3$, washing the solution with water and concentrating the chloroform layer in a vacuum desiccator to produce a viscous fluid free of acetic acid. The viscous fluid was analyzed by infrared spectroscopy which showed absorptions at 3330 to 3340 cm$^{-1}$ for secondary amide NH stretching, 1650 cm$^{-1}$ for tertiary amide carbonyl stretching, 1630 cm$^{-1}$ for secondary amide carbonyl stretching and 1550 cm$^{-1}$ for secondary amide II NH bending.

EXAMPLE 10

The preparation described in Example 7 was repeated except that (CF$_3$CO)$_2$O was used instead of (C$_6$H$_5$CO)$_2$O. The resulting fluid has a viscosity of 1372 centipoise, an A.N.E.=7800 (indicating that only 77% of the amine radicals had been acylated). Infrared spectroscopy of the product showed the presence of amide NH stretching at 3340 to 3330 cm$^{-1}$, carbonyl stretching for

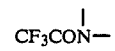

at 1730 cm$^{-1}$ and for

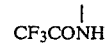

at 1680 cm$^{-1}$ and amide NH bending at 1540 cm$^{-1}$. Nuclear magnetic resonance spectroscopy showed the disappearance of the —NH signal at 1.7δ that ws present in the starting material. The product therefore was an equilibrium mixture of Me$_3$SiO$_{1\frac{1}{2}}$, Me$_2$SiO$_{2/2}$, and

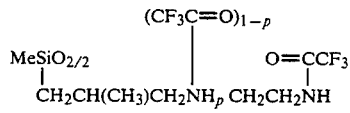

siloxane units, where p has a value of about 0.5.

That which is claimed is:

1. An organopolysiloxane compound containing at least one siloxane unit selected from siloxane units having the formulae

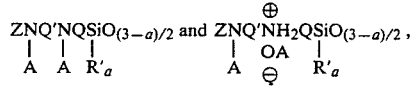

all other siloxane units in the organopolysiloxane compound being selected from siloxane units have the formulae

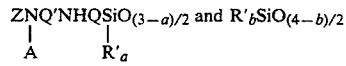

wherein, at each occurrence, Z denotes H or R", R" denotes a monovalent hydrocarbon radical, R' denotes a monovalent radical selected from hydrocarbon radicals, halogenated hydrocarbon radicals, hydrogen atoms, —OR" radicals, —OH radicals and —OA radicals, Q and Q' each denote a divalent hydrocarbon radical, A denotes an acyl radical having the formula

R denotes a monovalent hydrocarbon radical or a halogenated monovalent hydrocarbon radical, a has a value of 0, 1 or 2 and b has a value of 0, 1, 2 or 3.

2. An organopolysiloxane compound according to claim 1 wherein each Z denotes H and each Q' denotes —CH$_2$CH$_2$—.

3. An organopolysiloxane compound according to claim 2 wherein each R' contains no more than 6 carbon atoms and each R contains from 1 to 6 carbon atoms, inclusive.

4. An organopolysiloxane compound according to claim 3 consisting of two or more siloxane units selected from siloxane units having the formulae

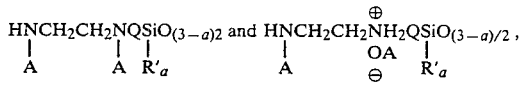

and, optionally, one or more siloxane units having the formula

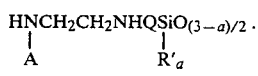

5. An organopolysiloxane compound according to claim 4 having the average formula

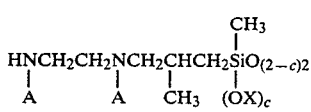

wherein c has an average value of from 0 to 1 and X denotes a radical selected from H, R″ or A.

6. An organopolysiloxane compound according to claim 5 wherein each A denotes

7. An organopolysiloxane compound according to claim 3 consisting of at least one siloxane unit having the formula

and at least one siloxane unit have the formula $R'_bSiO_{(4-b)/2}$.

8. An organopolysiloxane compound according to claim 7 having the formula

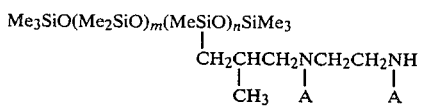

wherein each Me denotes —CH₃, m has an average value of from 0 to 10,000 and n has an average value of from 1 to 10,000.

9. An organopolysiloxane compound according to claim 8 wherein n has an average value of 1 for values of m less than 20 and an average value of from 1 to about 0.05 m for values of m equal to or greater than 20.

10. An organopolysiloxane compound according to claim 9 wherein each A denotes

11. An organopolysiloxane compound according to claim 3 consisting of at least one siloxane unit having the formula

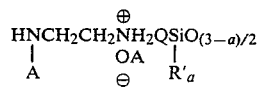

and at least one siloxane unit having the formula $R'_bSiO_{(4-b)/2}$.

12. An organopolysiloxane compound according to claim 11 having the formula

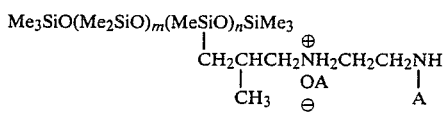

wherein each Me denotes —CH₃, m has an average value of from 0 to 10,000 and n has an average value of from 1 to 10,000.

13. An organopolysiloxane compound according to claim 12 wherein n has an average value of 1 for values of m less than 20 and an average value of from 1 to about 0.05 m for values of m equal to or greater than 20.

14. An organopolysiloxane compound according to claim 13 wherein each A denotes

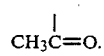

15. A process for preparing an organopolysiloxane compound containing at least one siloxane unit selected from siloxane units having the formulae

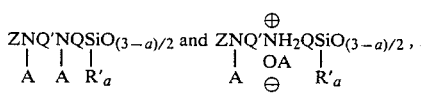

all other siloxane units in the organopolysiloxane compound being selected from siloxane units have the formulae

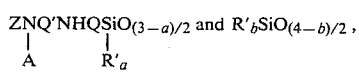

said process comprising:
(I) mixing components comprising
  (i) an amine-containing organopolysiloxane compound containing at least one siloxane unit having the formula

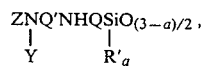

all other siloxane units in the amine-containing organopolysiloxane compound having the formula $R'_bSiO_{(4-b)/2}$ and
  (ii) a monocarboxylic acid anhydride having the formula A₂O, the amounts of component (i) and component (ii) being sufficient to provide at least one mol of component (ii) for every mol of component (i) and for every siloxane unit, exceeding one, having the formula

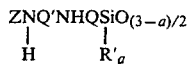

in the average molecule of component (i) wherein, at each occurrence, Z denotes H or R″, R″ denotes a monovalent hydrocarbon radical, R′ denotes a monovalent radical selected from hydrocarbon radicals, halogenated hydrocarbon radicals, hydrogen atoms, —OR″ radicals, —OH radicals and —OA radicals, Q and Q′ each denote a divalent hydrocarbon radical, A denotes an acyl radical having the formula

R denotes a monovalent hydrocarbon radical or a halogenated monovalent hydrocarbon radical, Y denotes H or A, a has a value of 0, 1 or 2 and b has a value of 0, 1, 2 or 3, and (II) maintaining the mixture of (I) at a temperature of from 0° C. to 300° C. for a length of time sufficient for the formation of at least one siloxane unit selected from siloxane units having the formulae

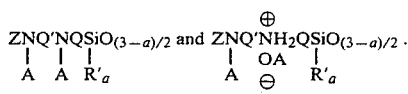

16. A process according to claim 15 wherein each Z and each Y denotes H and Q′ denotes —CH$_2$CH$_2$—.

17. A process according to claim 16 wherein the amounts of component (i) and component (ii) that are mixed are sufficient to provide substantially one mol of component (ii) for every siloxane unit having the formula

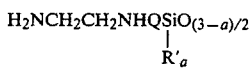

in the average molecule of component (i) and the resulting mixture is maintained at a temperature of from 50° to 150° C. until substantially all of said siloxane units have been fully modified.

18. A process according to claim 17 wherein component (i) has the formula

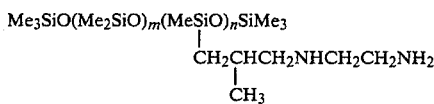

wherein each Me denotes —CH$_3$, m has an average value of from 0 to 10,000 and n has an average value of from 1 to 10,000.

19. A process according to claim 18 wherein n has an average value of 1 for values of m less than 20 and an average value of from 1 to about 0.05 m for values of m equal to or greater than 20.

20. A process according to claim 19 wherein component (ii) is acetic anhydride and said mixing is done under substantially anhydrous conditions and at room temperature.

21. A process according to claim 20 further comprising removing water, acetic acid and any unreacted acetic anhydride, from the product of the process by a process comprising distillation at a temperature of at least 120° C. thereby providing a residue which comprises organopolysiloxane compounds having the formulae

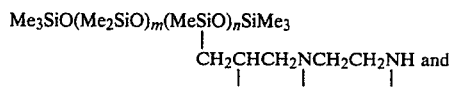

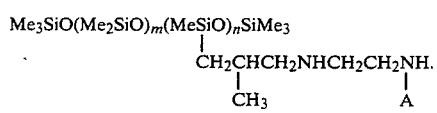

22. A process according to claim 16 wherein the amounts of component (i) and component (ii) that are mixed are sufficient to provide at least two mols of component (ii) for every siloxane unit having the formula

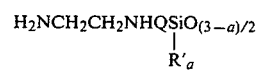

in the average molecule of component (i) and the resulting mixture is maintained at a temperature of from 50° to 150° C. until substantially all of said siloxane units have been fully acylated.

23. A process according to claim 22 wherein component (i) has the formula

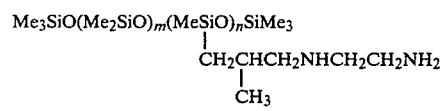

and the silicon-containing product of the process has the formula

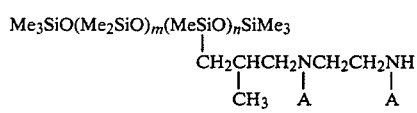

wherein each Me denotes —CH$_3$, m has an average value of from 0 to 10,000 and n has an average value of from 1 to 10,000.

24. A process according to claim 23 wherein n has an average value of 1 for values of m less than 20 and an average value of from 1 to about 0.05 m for values of m equal to or greater than 20.

25. A process according to claim 24 wherein component (ii) is acetic anhydride and said mixing is done under substantially anhydrous conditions and at room temperature.

26. A process according to claim 24 further comprising removing acetic acid and any unreacted acetic anhydride, from the fully acylated reaction product of the process.

27. The residue comprising organopolysiloxane compounds having the formulae

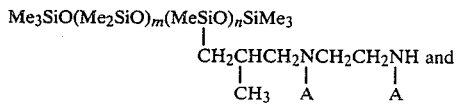

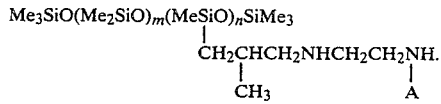

obtained by the process of claim 21.

28. A process according to claim 17 wherein component (ii) is acetic anhydride and the process further comprises removing water, acetic acid and any unreacted acetic anhydride from the product of the process by a process comprising distillation at a temperature of at least 120° C. thereby providing a residue which comprises an acylated organopolysiloxane compound containing siloxane units having the formulae

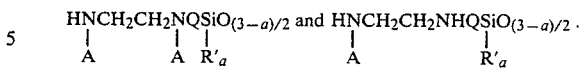

29. The acylated organopolysiloxane compound-containing residue produced by the process of claim 28.

30. A process according to claim 22 wherein component (ii) is acetic anhydride and the process further comprises removing acetic acid, and any unreacted acetic anhydride from the fully acylated reaction product.

31. The fully acylated reaction product obtained by the process of claim 30.

32. The fully acylated reaction product obtained by the process of claim 26.

33. The fully modified reaction product obtained by the process of claim 20.

* * * * *

UNITED STATES PATENT AND TRADEMARK OFFICE
CERTIFICATE OF CORRECTION

PATENT NO. : 4,507,455

DATED : March 26, 1985

INVENTOR(S) : Thomas J. Tangney and Maris J. Ziemelis

It is certified that error appears in the above-identified patent and that said Letters Patent is hereby corrected as shown below:

In Col. 4, line 53, delete "$\underset{\underset{A}{|}}{H}NCH_2CH_2\underset{\underset{\ominus}{OA}}{\overset{\oplus}{N}H_2}CH_2\underset{\underset{CH_3}{|}}{C}H\underset{\underset{R'_2}{|}}{C}H_2SiO_{(3-a)/2}$"

and substitute therefor -- $\underset{\underset{A}{|}}{H}NCH_2CH_2\underset{\underset{\ominus}{OA}}{\overset{\oplus}{N}H_2}CH_2\underset{\underset{CH_3}{|}}{C}H\underset{\underset{R'_a}{|}}{C}H_2SiO_{(3-a)/2}$ --

In Col. 8, line 1, delete "$R''Me_2SiO(MeR'SiO)_m(Me\underset{\underset{\underset{A}{|}}{Q}NCH_2CH_2\underset{\underset{A}{|}}{N}H}{\overset{|}{S}}iO)_nSiMe_2R''$"

and substitute therefor -- $R''Me_2SiO(MeR''SiO)_m(Me\underset{\underset{\underset{A}{|}}{Q}NCH_2CH_2\underset{\underset{A}{|}}{N}H}{\overset{|}{S}}iO)_nSiMe_2R''$ --

In Col. 14, line 21, delete "$\underset{\underset{H}{|}}{N}HCH_2CH_2\underset{\underset{\ominus}{OA}}{\overset{\oplus}{N}H_2}Q\underset{\underset{R'_a}{|}}{S}iO_{(3-a)/2}$"

and substitute therefor -- $\underset{\underset{A}{|}}{N}HCH_2CH_2\underset{\underset{\ominus}{OA}}{\overset{\oplus}{N}H_2}Q\underset{\underset{R'_a}{|}}{S}iO_{(3-a)/2}$ --

In Col. 19, line 35, delete $\underset{"CH_3\overset{|}{C}=O"}{-NH}$ and substitute therefor -- $\underset{C\underline{H}_3\overset{|}{C}=O}{-NH}$ --.

UNITED STATES PATENT AND TRADEMARK OFFICE
CERTIFICATE OF CORRECTION

PATENT NO. : 4,507,455      Page 2 of 3

DATED : March 26, 1985

INVENTOR(S) : Thomas J. Tangney and Maris J. Ziemelis

It is certified that error appears in the above-identified patent and that said Letters Patent is hereby corrected as shown below:

In Col. 19, line 42, delete "$CH_3\overset{-N-}{\underset{|}{C}}=O$" and substitute therefor -- $\underline{CH_3}\overset{-N-}{\underset{|}{C}}=O$ --.

In Col. 19, line 58, delete "ration" and substitute therefor -- ratio --.

In Col. 20, line 55, delete "$SiO_{178}$" and substitute therefor -- $SiO_{1/2}$ --.

In Col. 21, line 20, delete $$\underset{\underset{C_6H_5C=O \quad\quad O=CC_6H_5}{CH_2CH(CH_3)CH_2\underset{|}{N}CH_2\ CH_2\underset{|}{N}H}}{Me\underset{|}{Si}O_{2/2}}$$

and substitute therefor $$\underset{\underset{C_6H_5C=O \quad\quad O=CC_6H_5}{-- CH_2CH(CH_3)CH_2\underset{|}{N}CH_2CH_2\underset{|}{N}H --}}{Me\underset{|}{Si}O_{2/2}}$$

In Col. 22, line 19, delete "$Me_3SiO_{178}$" and substitute therefor -- $Me_3SiO_{1/2}$ --.

UNITED STATES PATENT AND TRADEMARK OFFICE
CERTIFICATE OF CORRECTION

PATENT NO. : 4,507,455

DATED : March 26, 1985

INVENTOR(S) : Thomas J. Tangney and Maris J. Ziemelis

It is certified that error appears in the above-identified patent and that said Letters Patent is hereby corrected as shown below:

In Col. 23, line 22, delete "$\text{HNCH}_2\text{CH}_2\text{NCH}_2\text{CHCH}_2\overset{\overset{\text{CH}_3}{|}}{\text{Si}}\text{O}_{(2-c)2}$"
$$\phantom{HNCH_2CH_2NCH_2CHCH_2} \underset{A}{|} \phantom{CH_2} \underset{A}{|} \phantom{CHCH_2} \underset{\text{CH}_3\ (\text{OX})_c}{}$$

and substitute therefor -- $\text{HNCH}_2\text{CH}_2\text{NCH}_2\text{CHCH}_2\overset{\overset{\text{CH}_3}{|}}{\text{Si}}\text{O}_{(2-c)/2}$ --
$$\phantom{HNCH_2CH_2NCH_2CHCH_2} \underset{A}{|} \phantom{CH_2} \underset{A}{|} \phantom{CHCH_2} \underset{\text{CH}_3\ (\text{OX})_c}{}$$

In Col. 26, line 62, delete "24" and substitute therefor -- 25 --.

Signed and Sealed this

Twenty-ninth Day of October 1985

[SEAL]

Attest:

DONALD J. QUIGG

Attesting Officer

Commissioner of Patents and Trademarks—Designate